US010406381B2

(12) United States Patent
Subramanian

(10) Patent No.: US 10,406,381 B2
(45) Date of Patent: *Sep. 10, 2019

(54) MULTI-BALLOON CATHETER FOR MEDICAL APPLICATIONS

(71) Applicant: BEST MEDICAL INTERNATIONAL, INC., Springfield, VA (US)

(72) Inventor: Manny Subramanian, Frederick, MD (US)

(73) Assignee: Best Medical International, Inc., Springfield, VA (US)

( * ) Notice: Subject to any disclaimer, the term of this patent is extended or adjusted under 35 U.S.C. 154(b) by 174 days.

This patent is subject to a terminal disclaimer.

(21) Appl. No.: 15/189,396

(22) Filed: Jun. 22, 2016

(65) Prior Publication Data

US 2016/0339266 A1    Nov. 24, 2016

Related U.S. Application Data

(62) Division of application No. 12/889,032, filed on Sep. 23, 2010, now Pat. No. 9,402,980.

(51) Int. Cl.
*A61N 5/10* (2006.01)
*A61M 25/00* (2006.01)
*A61M 25/10* (2013.01)

(52) U.S. Cl.
CPC ....... *A61N 5/1002* (2013.01); *A61M 25/0017* (2013.01); *A61M 25/1011* (2013.01);
(Continued)

(58) Field of Classification Search
CPC .......... A61M 25/0017; A61M 25/1011; A61M 2210/1067; A61M 25/10181;
(Continued)

(56) References Cited

U.S. PATENT DOCUMENTS 2,799,273 A * 7/1957 Oddo ................. A61M 25/1011
604/101.05
4,976,266 A    12/1990 Huffman et al.
(Continued)

FOREIGN PATENT DOCUMENTS

JP     2009232882    10/2009
WO    WO99/27985    6/1999
(Continued)

OTHER PUBLICATIONS

Astro 2015 Annual Meeting, Ancer Medical, Hialeah, FL, Booth: 489, Print Profile, Oct. 2015, 2 pages.
(Continued)

*Primary Examiner* — Navin Natnithithadha
*Assistant Examiner* — Sunita Reddy

(57) ABSTRACT

According to one general aspect, there is a multi-balloon catheter for medical applications that includes a multi-balloon inflator that inflates multiple balloons on a single catheter, an extraction point used to remove human fluids from the human body, and a connecting point that allows a syringe or a machine to insert air or any other liquid, such as a liquid saline solution, for inflation of a corresponding balloon of the multiple balloons or insert radioactive isotopes into the multi-balloon inflator.

34 Claims, 8 Drawing Sheets

(52) U.S. Cl.
CPC ..... *A61M 25/10181* (2013.11); *A61N 5/1071* (2013.01); *A61M 2210/1067* (2013.01); *A61M 2210/1089* (2013.01); *A61N 2005/1003* (2013.01); *A61N 2005/1004* (2013.01); *A61N 2005/1018* (2013.01); *A61N 2005/1021* (2013.01)

(58) Field of Classification Search
CPC ... A61M 2210/1089; A61N 2005/1004; A61N 2005/1003; A61N 5/1071; A61N 5/1002; A61N 2005/1018; A61N 2005/1021
USPC .......................................... 600/1, 3; 604/328
See application file for complete search history.

(56) References Cited

U.S. PATENT DOCUMENTS

| | | | |
|---|---|---|---|
| 5,623,940 | A | 4/1997 | Daikuzono |
| 5,653,683 | A | 8/1997 | D'Andrea |
| 5,720,717 | A | 2/1998 | D'Andrea |
| 5,782,800 | A * | 7/1998 | Yoon ................ A61B 17/00234 600/207 |
| 5,913,813 | A | 6/1999 | Williams et al. |
| 6,119,697 | A | 9/2000 | Engel et al. |
| 6,251,059 | B1 | 6/2001 | Apple et al. |
| 6,348,039 | B1 * | 2/2002 | Flachman ................ A61B 5/01 600/486 |
| 6,422,997 | B1 * | 7/2002 | Green ............... A61M 25/0075 600/207 |
| 6,434,418 | B1 * | 8/2002 | Neal .................. A61B 5/02411 600/376 |
| 6,447,462 | B1 | 9/2002 | Wallace et al. |
| 6,616,629 | B1 | 9/2003 | Verin et al. |
| 6,923,754 | B2 | 8/2005 | Lubock |
| 6,955,641 | B2 | 10/2005 | Lubock |
| 6,958,052 | B1 | 10/2005 | Charlton |
| 7,357,770 | B1 | 4/2008 | Cutrer et al. |
| 7,662,082 | B2 | 2/2010 | White et al. |
| 8,251,884 | B2 | 8/2012 | Lubock et al. |
| 8,277,370 | B2 | 10/2012 | Quick |
| 8,287,442 | B2 | 10/2012 | Quick |
| 8,348,825 | B2 | 1/2013 | Partridge et al. |
| 8,360,950 | B2 | 1/2013 | Acosta et al. |
| 8,568,284 | B2 | 10/2013 | White et al. |
| 8,961,383 | B2 | 2/2015 | Parsai et al. |
| 9,283,402 | B2 | 3/2016 | Cutrer |
| 9,402,980 | B2 | 8/2016 | Subramanian |
| 9,498,644 | B2 | 11/2016 | Cutrer |
| 2003/0032851 | A1 | 2/2003 | Apple et al. |
| 2004/0087827 | A1 | 5/2004 | Lubock |
| 2005/0027157 | A1 | 2/2005 | Winkler et al. |
| 2005/0080313 | A1 | 4/2005 | Stewart et al. |
| 2005/0101824 | A1 | 5/2005 | Stubbs |
| 2006/0100475 | A1 | 5/2006 | White et al. |
| 2006/0173233 | A1 | 8/2006 | Lovoi |
| 2006/0212022 | A1 | 9/2006 | Gellman |
| 2007/0106108 | A1 | 5/2007 | Hermann et al. |
| 2007/0167666 | A1 | 7/2007 | Lubock et al. |
| 2008/0221384 | A1 | 9/2008 | Chi Sing et al. |
| 2009/0082609 | A1 * | 3/2009 | Condado ........... A61M 25/0075 600/4 |
| 2009/0143634 | A1 | 6/2009 | Benson et al. |
| 2009/0198095 | A1 | 8/2009 | Acosta et al. |
| 2009/0254064 | A1 | 10/2009 | Boatman |
| 2009/0264696 | A1 | 10/2009 | White et al. |
| 2009/0312593 | A1 | 12/2009 | Drobnik et al. |
| 2010/0069878 | A1 | 3/2010 | Parsai et al. |
| 2010/0191034 | A1 | 7/2010 | Cutrer et al. |
| 2010/0331601 | A1 | 12/2010 | Partridge et al. |
| 2011/0034976 | A1 | 2/2011 | Mon et al. |
| 2012/0253099 | A1 | 10/2012 | Mon et al. |
| 2014/0257092 | A1 | 9/2014 | Lamoureux et al. |
| 2014/0275712 | A1 * | 9/2014 | D'Andrea ............ A61N 5/1028 600/2 |

FOREIGN PATENT DOCUMENTS

| | | |
|---|---|---|
| WO | WO2008124149 | 10/2008 |
| WO | WO2013049827 | 4/2013 |

OTHER PUBLICATIONS

Gilad N. Cohen et al., "Design of a Novel Applicator for Esophageal High Dose Rate Brachytherapy", Abstract PO51, Abstracts / Brachytherapy, vol. 14, 2015, pp. S101-S102.

"What is Esophageal Brachytherapy" Ancer Medical, Available at: http://www.ancermedical.com/wp-content/uploads/2016/04/Esophageal-Applicator.pdf, 2016, 6 pages.

Esophageal Applicator (E-AppTM), Ancer Medical, 2016, 1 page.

Anorectal Applicator (AR) TM, Ancer Medical, 2016, 2 pages.

Esophageal Applicator (E-App)TM, Ancer Medical, Available at: http://www.ancermedical.com/wp-content/uploads/2016/04/Esophageal-Applicator.pdf, 2016, 5 pages.

"Hologic takes SenoRx assets in out-of-court settlement with C.R. Bard", A. Sarvestani, www.massdevice.com, Aug. 14, 2013 (downloaded,Oct. 19, 2015), 4 pages.

"Best Dual Balloon Breast Brachytherapy Applicator", from TeamBest brochure/material, Sep. 13, 2014, 3 pages.

U.S. Appl. No. 15/292,923, filed Oct. 13, 2016, Subramanian.
U.S. Appl. No. 15/293,342, filed Oct. 14, 2016, Subramanian.
U.S. Appl. No. 12/889,032, filed Sep. 23, 2010, Subramanian.

* cited by examiner

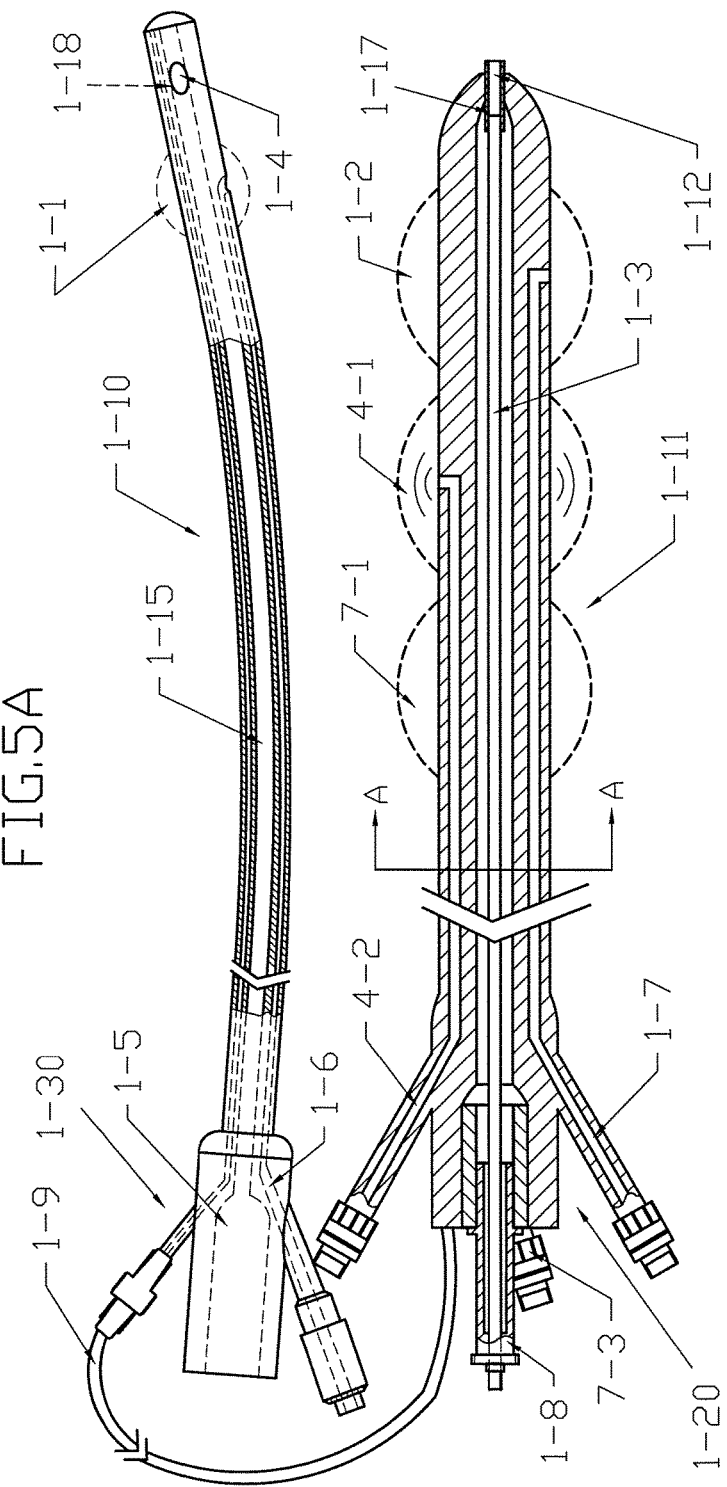
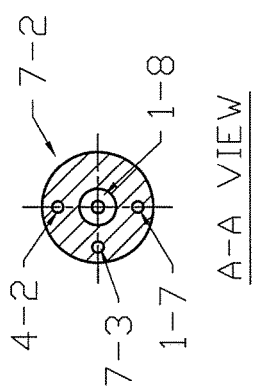
FIG.5A
FIG.5B  A-A VIEW

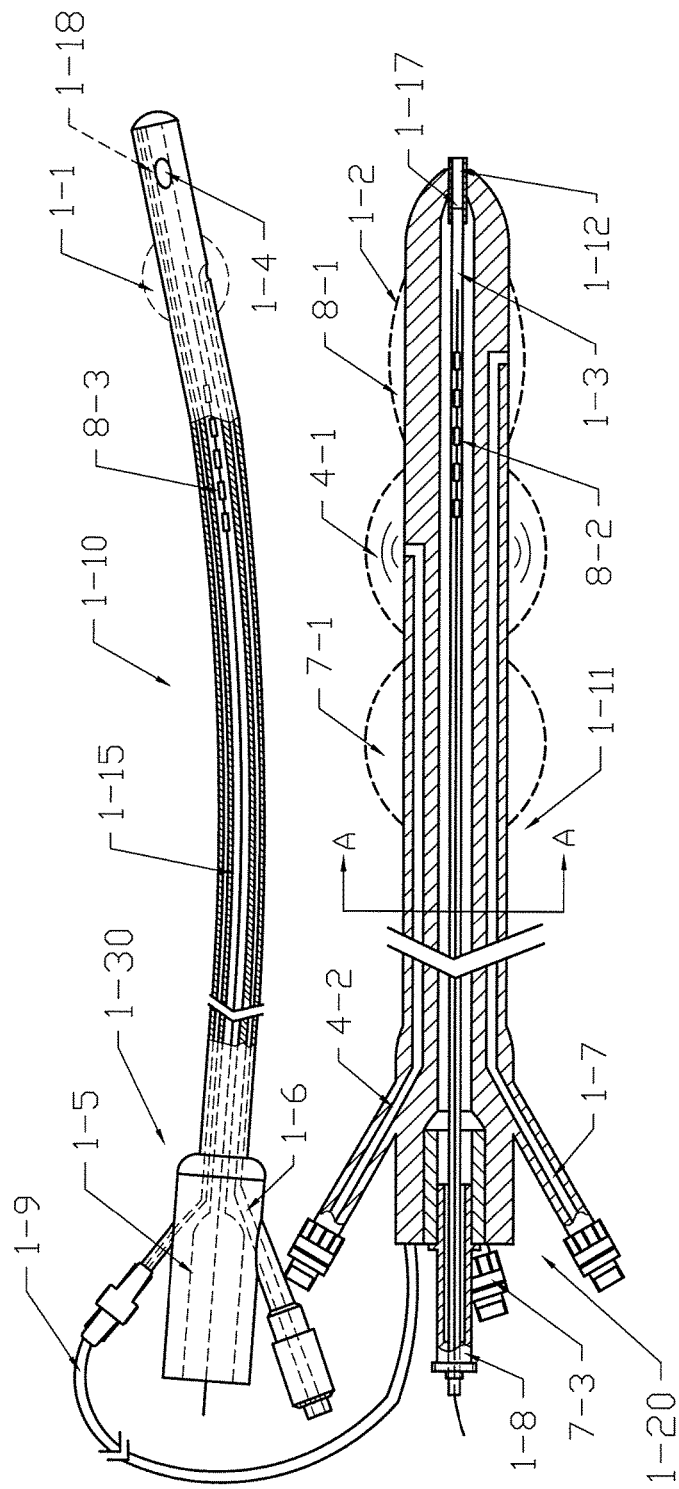
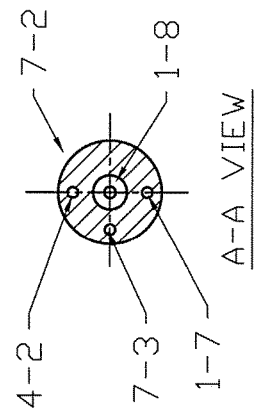

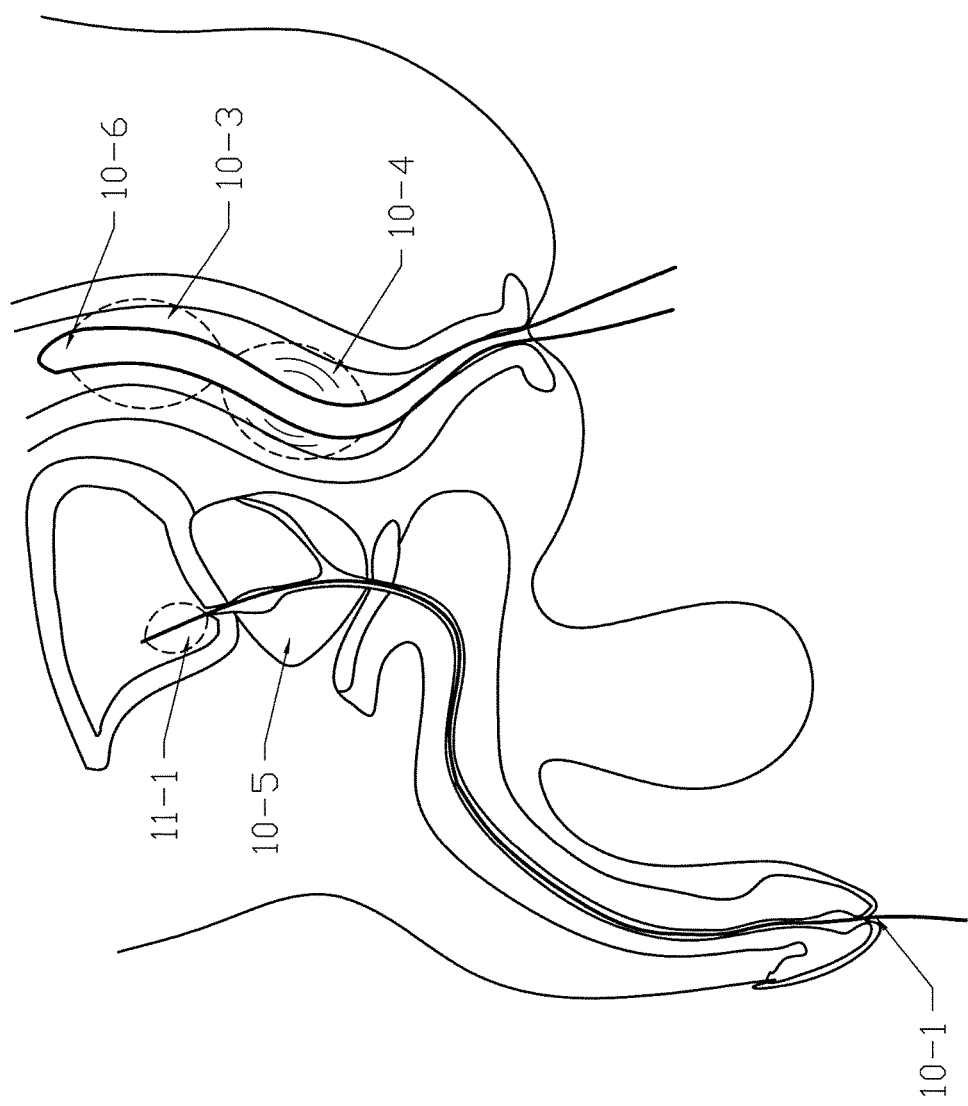

MULTI-BALLOON CATHETER FOR MEDICAL APPLICATIONS

CROSS REFERENCE TO RELATED APPLICATION

This application claims priority under 35 U.S.C. § 120 to and is a divisional application of U.S. patent application Ser. No. 12/889,032, filed on Sep. 23, 2010, hereby incorporated herein by reference in its entirety.

FIELD OF THE INVENTION

The invention is related to a medical device and, more particularly, a multi-purpose intra-cavity catheter that is used to deliver dose, measure the dose and remove human waste while providing an easy connection module.

BACKGROUND

In medicine, a catheter is a tube that can be inserted into a body cavity, duct, or vessel. Catheters thereby allow drainage, injection of fluids, or access by surgical instruments. The process of inserting a catheter is catheterization. In most uses, a catheter is a thin, flexible tube ("soft" catheter), though in some uses, it is a larger, solid ("hard") catheter. A catheter left inside the body, either temporarily or permanently, may be referred to as an indwelling catheter. A permanently inserted catheter may be referred to as a permcath.

The ancient Syrians created catheters from reeds. "Katheter- καθετήρ" originally referred to an instrument that was inserted such as a plug. The word "katheter" in turn came from "kathiemai- καθίεμαι" meaning "to sit". The ancient Greeks inserted a hollow metal tube through the urethra into the bladder to empty it and the tube came to be known as a "katheter".

Prior catheters were used only for single functions, such as removing human remains and enlarging an area inside the human body. The single functioning catheters require that medical personnel remove one catheter and insert another catheter into the patient when multiple functions are required to be performed on the patient. This removal and insertion process creates much discomfort to the patient, because the removal of one catheter and insertion of another catheter creates pain. Also, when multiple catheters need to be inserted into a patient, each catheter is inserted into the patient. However, the catheter's excessive length can cause confusion and the medical personnel may perform a function on the wrong catheter.

Thus, the need exists to have a catheter that can provide multiple functions and which is less traumatic than current procedures involving insertion and removal. The present invention meets that need without the risk of causing damage or producing pain.

SUMMARY OF THE INVENTION

According to one general aspect, there is a medical device including a locking mechanism that is used to connect a plurality of catheters, a multi-balloon inflator that inflates multiple balloons on a single catheter, an extraction point used to remove bodily fluids, e.g. human fluids from the human body, and a connecting point that allows a syringe or a machine to insert air or a liquid, such as a liquid saline solution, or to insert radioactive isotopes into the multi-balloon inflator. Also, a multi-balloon catheter for medical applications is provided that includes a multi-balloon inflator that inflates multiple balloons on a single catheter, an extraction point used to remove human fluids from the human body, and a connecting point that allows a syringe or a machine to insert air or any other liquid, such as a liquid saline solution, for inflation of a corresponding balloon of the multiple balloons. By allowing each balloon to have its respective connection, an advantage of such connection is that it will allow medical personnel to control the size of each balloon independently. Further, by having multiple balloons on a single catheter the shape of each balloon can be changed relative to the location of the catheter in the human body to allow for a proper fixture, such as in a body cavity.

The medical device that contains the locking mechanism can be affixed to any male or female connection attached to any type of catheter.

The medical device of the multi-balloon catheter that contains the multi-balloon inflator is connected to each individual connecting point to allow a volume for inflation.

The medical device that contains the said locking mechanism when affixed to another catheter creates a vacuum seal that does not allow the fluids or any air to pass through any said connecting point.

The medical device that contains the extraction point contains an inner seal within the opening that only allows for a single direction flow for only removal of fluids which does not allow for fluids to be inserted into the human body.

The medical device that contains the extraction point is large enough to contain a measuring device used to measure the amount of dose radiated to human tissue while said extraction point is removing fluids from the human body.

The medical device contains a multi-balloon inflator that includes a plurality of connections, wherein at least one connection of the multi-balloon inflator contains radioactive isotopes while the remaining one or more connections of the multi-balloon inflator contain air or any other liquid, such as a liquid saline solution, for inflation of the corresponding balloon.

The medical device that contains a plurality of catheters can be inserted into both the rectum and the urethra with a plurality of measuring devices to take dose measurements while applying dose therapy through the multi-balloon inflator.

According to another general aspect, there is a method of operating a multi-functional catheter, wherein said method comprises connecting a plurality of catheters, inflating multiple balloons on a single catheter, removing human fluids from the human body, and pumping liquid saline solution or radioactive isotopes into said multi-balloon inflator.

The connecting includes affixing any male or female connection to the catheter.

The inflating is provided to each individual connecting point to allow the volume for inflation.

The affixing to another catheter creates a vacuum seal that does not allow the fluids or any air to pass through any said connecting point.

The removing fluids by an inner seal within the opening that only allows for a single direction flow for only removal of fluids which does not allow for fluids to be inserted into the human body.

The removing includes a measuring device used to measure the amount of dose radiated to human tissue while the extraction point is removing bodily fluids, such as from the human body.

The radiating includes providing by a multi-balloon inflator through a corresponding connection radioactive isotopes, while the other one or more of the connections of the multi-balloon inflator contains air or any other liquid, such as a liquid saline solution, for inflation of the corresponding balloon on a medical device that contains a multi-balloon inflator having a plurality of connections.

A plurality of said medical devices can be inserted into both the rectum and urethra with a plurality of said measuring devices take dose measurements while applying dose therapy through said multi-balloon inflator.

DESCRIPTION OF THE DRAWINGS

FIG. 5A is an illustration of a rectum catheter including a first position rectum balloon, a second position radiation balloon and a third position rectum balloon attached to a urethra catheter that includes a first position urethra catheter balloon. FIG. 5B is a sectional view of the rectum catheter 1-11 taken at the section A-A of FIG. 5A.

FIG. 6A is an illustration of a rectum catheter including a first position rectum balloon, a second position radiation balloon, a third position rectum balloon and a measuring device, such as a metal-oxide-semiconductor field-effect transistor (MOSFET), attached to a urethra catheter that includes a measuring device and a first position urethra catheter balloon. FIG. 6B is a sectional view of the rectum catheter 1-11 taken at the section A-A of FIG. 6A.

FIG. 8 is an illustration of a rectum catheter including a first position rectum balloon and a second position rectum balloon attached to a urethra catheter that includes a first position urethra catheter balloon.

Figure 1:
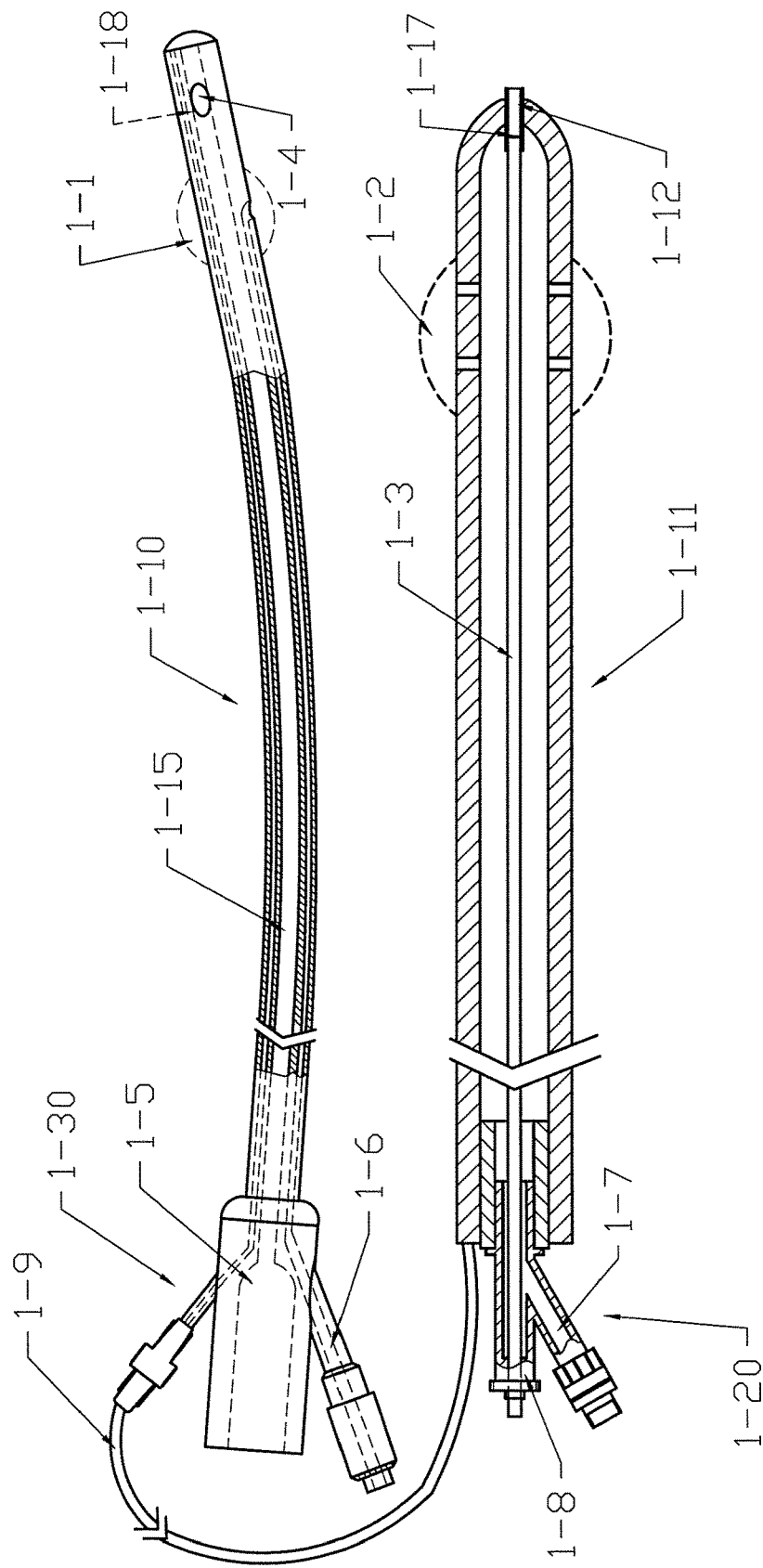
FIG. 1 is an illustration of a first position rectum balloon attached to a rectum catheter and a first position urethra catheter balloon attached to a urethra catheter.

Throughout the drawings and the detailed description, unless otherwise described, the same drawing reference numerals will be understood to refer to the same elements, features, and structures. The relative size and depiction of these elements may be exaggerated for clarity, illustration, and convenience.

DETAILED DESCRIPTION

The following detailed description is provided to assist the reader in gaining a comprehensive understanding of the methods, apparatuses and/or systems described herein. Accordingly, various changes, modifications, and equivalents of the systems, apparatuses, and/or methods described herein will likely suggest themselves to those of ordinary skill in the art. Also, descriptions of well-known functions and constructions are omitted to increase clarity and conciseness.

FIG. 1 shows an exemplary medical device including a rectum catheter 1-11 that includes a first position rectum balloon 1-2, as well as a balloon inflator 1-20 having connections 1-7 and 1-8; the rectum catheter 1-11 being attached to a urethra catheter 1-10, the urethra catheter 1-10 including a urethra catheter balloon 1-1, as well as a balloon inflator 1-30 having connections 1-5 and 1-6. The rectum catheter 1-11 that includes the rectum balloon 1-2 has multiple uses and features. The rectum balloon 1-2 can be used to deliver radiation, such as by radioactive isotopes that can be inserted via the connection 1-7, and a measuring device, e.g., a sensor, (not shown in FIG. 1), as can be associated with the rectum catheter 1-11 or with the urethra catheter 1-10, that can simultaneously measure the radiation that is being delivered to the abnormal growth and a connection of the rectum catheter 1-11 can remove bodily fluids, e.g., human waste. The rectum catheter 1-11 has a female or a male connection 1-8 of a balloon inflator 1-20 that is used to insert any form of a sensor for dose measurement and simultaneously remove human waste by an extraction opening 1-12 in the rectum catheter 1-11. The extraction opening 1-12 contains an inner seal 1-17 that only allows for a single direction flow for removal of bodily fluids and does not allow for fluids to be inserted into a body cavity, such as the rectum. The human waste removed travels through a tube 1-3 that is associated with the male or female connection 1-8. Furthermore, the rectum catheter 1-11 has a luer lock connection 1-7 of the balloon inflator 1-20 that is used to inflate the rectum balloon 1-2 to a predetermined size. The balloon inflation of the rectum balloon 1-2 may be used as a locking mechanism for the rectum catheter 1-11 in the patient or can be used to push internal organs in a certain direction. The rectum catheter 1-11 may be attached by a locking mechanism 1-9 to the urethra catheter 1-10. The locking mechanism 1-9 may be attached by either a male or a female connection, and the locking mechanism 1-9 is associated with the balloon inflator 1-20 and the balloon inflator 1-30. The locking mechanism 1-9 allows for medical personnel to have an easier control of the rectum catheter 1-11 and the urethra catheter 1-10 to provide delivery and extraction guidance for the catheters within a single area. The urethra catheter 1-10 has a urine or bodily fluid extraction opening 1-4 that communicates with a tube 1-15 that is used to remove fluids in the bladder that are taken out by an extraction opening connection 1-5 of the balloon inflator 1-30 and by the associated tube 1-15. The extraction opening 1-4 contains an inner seal 1-18 that only allows for a single direction flow for removal of bodily fluids and does not allow for fluids to be inserted into a body cavity, such as the bladder. Furthermore, a measuring device (not shown in FIG. 1) may be inserted into the extraction opening connection 1-5 and into the tube 1-15 while removing the urine or bodily fluid. The advantage allows for simultaneously measuring a dose and removing urine by the urethra catheter 1-10. The urethra catheter balloon 1-1 is an inflatable balloon. The balloon inflation can be performed via a male or a female luer lock connection 1-6 of the balloon inflator 1-30 of the urethra catheter 1-10. Further drawings will show modifications to both the urethra catheter 1-11 and the rectum catheter 1-10.

Figure 2:
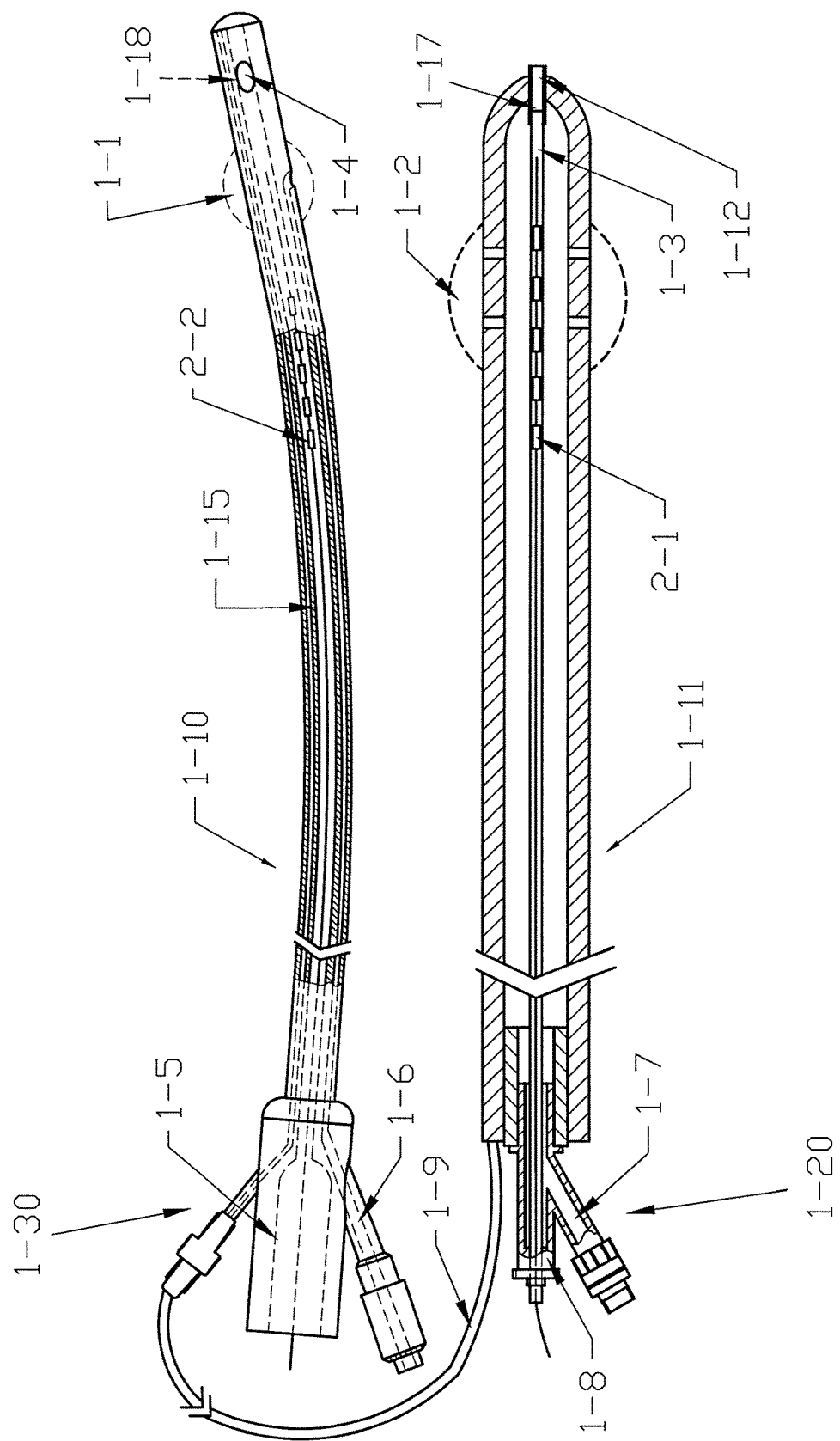
FIG. 2 is an illustration of a rectum catheter including a first position rectum balloon and a measuring device, such as a metal-oxide-semiconductor field-effect transistor (MOSFET), attached to a urethra catheter that includes a measuring device and a first position urethra catheter balloon.

FIG. 2 shows an exemplary medical device, similar to that shown in FIG. 1, including a rectum catheter 1-11 attached to a urethra catheter 1-10. Upon further review, the rectum catheter 1-11 allows for a measuring device 2-1 for dose measurement, such as a metal-oxide-semiconductor field-effect transistor (MOSFET), to be inserted into a center valve of a connection 1-8 of a balloon inflator 1-20 of the rectum catheter 1-11. The rectum catheter 1-11 may be attached by a locking mechanism 1-9 to the urethra catheter 1-10, as described. The advantage for inserting the measuring device 2-1 will allow medical personnel to measure the dose simultaneously while delivering the radiation to the tumor region. Furthermore, a second measuring device 2-2 may be inserted into the urethra catheter 1-10 through an extraction opening connection 1-5 of a balloon inflator 1-30 and into an associated tube 1-15 of the extraction opening connection 1-5. Inflating the rectum balloon 1-2 allows for determining the organ region and for providing a fixing or locking mechanism. The inflating rectum balloon 1-2 on the rectum catheter 1-11 can also be filled with a radioactive material, e.g., radioactive isotopes, via the connection 1-7 of the balloon inflator 1-20 that delivers dose while being measured by the measuring device 2-1. This is a big advantage since the dose can be measured and the volume of radioactive isotopes can be reduced depending on the inflating size of the inflating rectum balloon 1-2. Next, the second measuring device 2-2 can also be inserted into the urethra catheter 1-10 through the extraction opening connection 1-5 of the balloon inflator 1-30 into the associated tube 1-15 and, along with the measuring device 2-1 in the rectum catheter 1-11, can allow medical personnel to measure the dose from two different locations at the same time. Also, as described, the urethra catheter 1-10 has a urine extraction opening 1-4 that communicates with the tube 1-15 and is used to remove fluids in the bladder that are taken out by the extraction opening connection 1-5 of the balloon inflator 1-30 and by the associated tube 1-15. The extraction opening 1-4 contains an inner seal 1-18 that only allows for a single direction flow for removal of bodily fluids and does not allow for fluids to be inserted into a body cavity, such as the bladder. The rectum catheter 1-11 has a female or a male connection 1-8 of a balloon inflator 1-20, that can be used to insert any form of a sensor for dose measurement and simultaneously remove human waste by an extraction opening 1-12 in the rectum catheter 1-11. The extraction opening 1-12 contains an inner seal 1-17 that only allows for a single direction flow for removal of bodily fluids and does not allow for fluids to be inserted into a body cavity, such as the rectum. The human waste removed travels through a tube 1-3 associated with the male or female connection 1-8.

Figure 3:
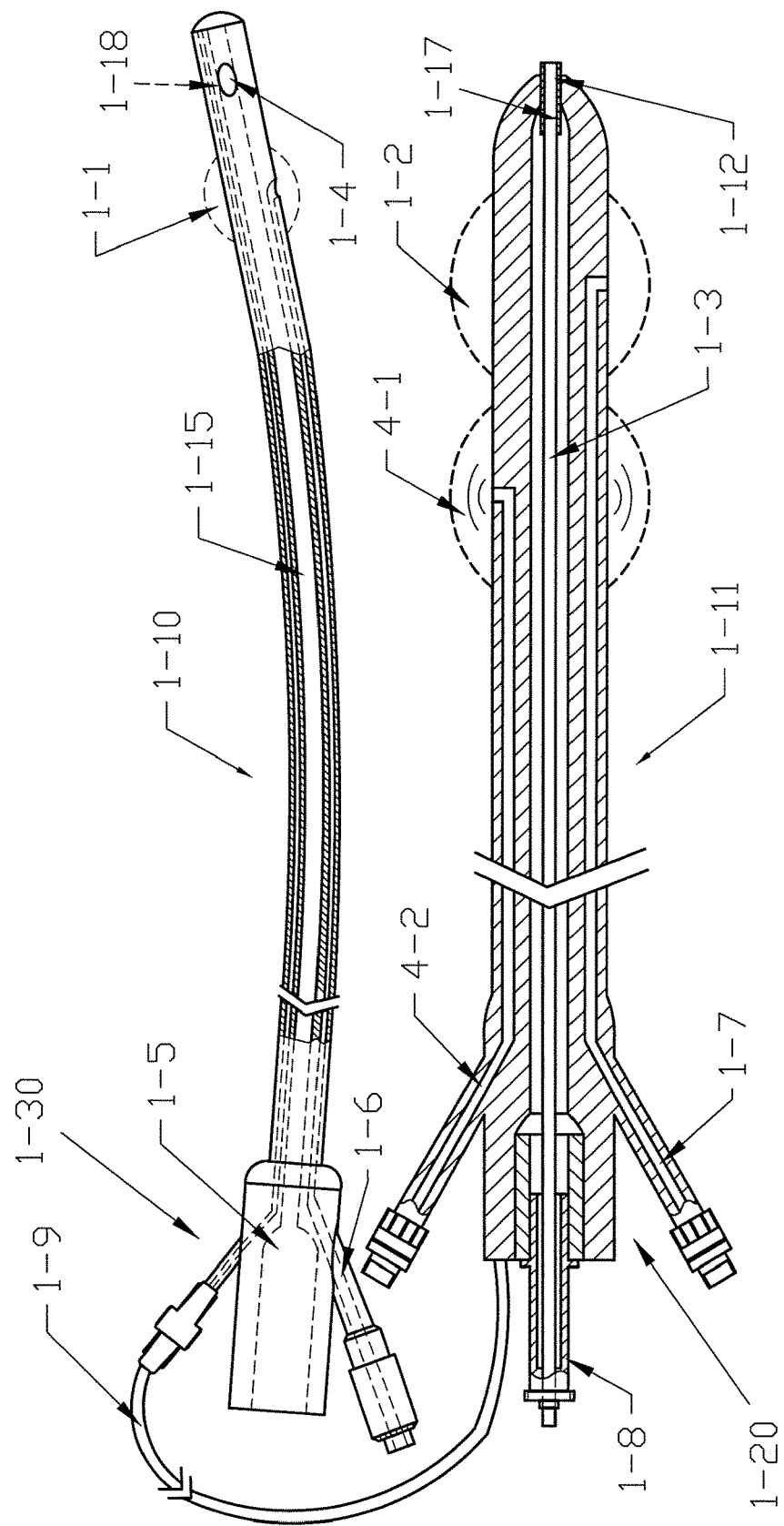
FIG. 3 is an illustration of a rectum catheter including a first position rectum balloon and a second position rectum balloon attached to a urethra catheter that includes a first position urethra catheter balloon.

FIG. 3 shows an exemplary medical device that includes a rectum catheter 1-11 attached to a urethra catheter 1-10. The rectum catheter 1-11 includes a first position rectum balloon 1-2 and second position rectum balloon 4-1, as well as a balloon inflator 1-20, as a multi-balloon inflator, having connections 1-7, 1-8 and 4-2; and the urethra catheter 1-10 includes a first position urethra catheter balloon 1-1, as well as a balloon inflator 1-30 having connections 1-5 and 1-6. The rectum catheter 1-11 may be attached by a locking mechanism 1-9 to the urethra catheter 1-10, as described. The rectum catheter 1-11 contains two balloons, which allows for the first position rectum balloon 1-2 to be used for fixing or locking. The second position rectum balloon 4-1 can be filled with a radioactive material, e.g. radioactive isotopes, via the connection 4-2. The second position rectum balloon 4-1 can deliver the radiation after the first position rectum balloon 1-2 has been inflated via the connection 1-7. Another advantage for double inflatable balloons can be the first position rectum balloon 1-2 can be used to move sensitive organs out of the region, and the second position rectum balloon 4-1 can deliver the dose. Each balloon has the ability to be filled up via its male or female connection. Specifically, the second position rectum balloon 4-1 is enlarged via the male/female connection 4-2; and, the first position rectum balloon 1-2 is enlarged via the male/female connection 1-7. By allowing each balloon to have its respective connection, an advantage of such connection is that it will allow medical personnel to control the size of each balloon independently. Also, as described, the urethra catheter 1-10 has a urine or bodily fluid extraction opening 1-4 that communicates with a tube 1-15 that is used to remove fluids in the bladder that are taken out by an extraction opening connection 1-5 of the balloon inflator 1-30 and the associated tube 1-15. The extraction opening 1-4 contains an inner seal 1-18 that only allows for a single direction flow for removal of bodily fluids and does not allow for fluids to be inserted into a body cavity, such as the bladder. The rectum catheter 1-11 has the female or a male connection 1-8 of the balloon inflator 1-20, that can be used to insert any form of a sensor for dose measurement and while removing human waste by an extraction opening 1-12 in the rectum catheter 1-11. The extraction opening 1-12 contains an inner seal 1-17 that only allows for a single direction flow for removal of bodily fluids and does not allow for fluids to be inserted into a body cavity, such as the rectum. The human waste removed travels through a tube 1-3 associated with the male or female connection 1-8.

Figure 4:
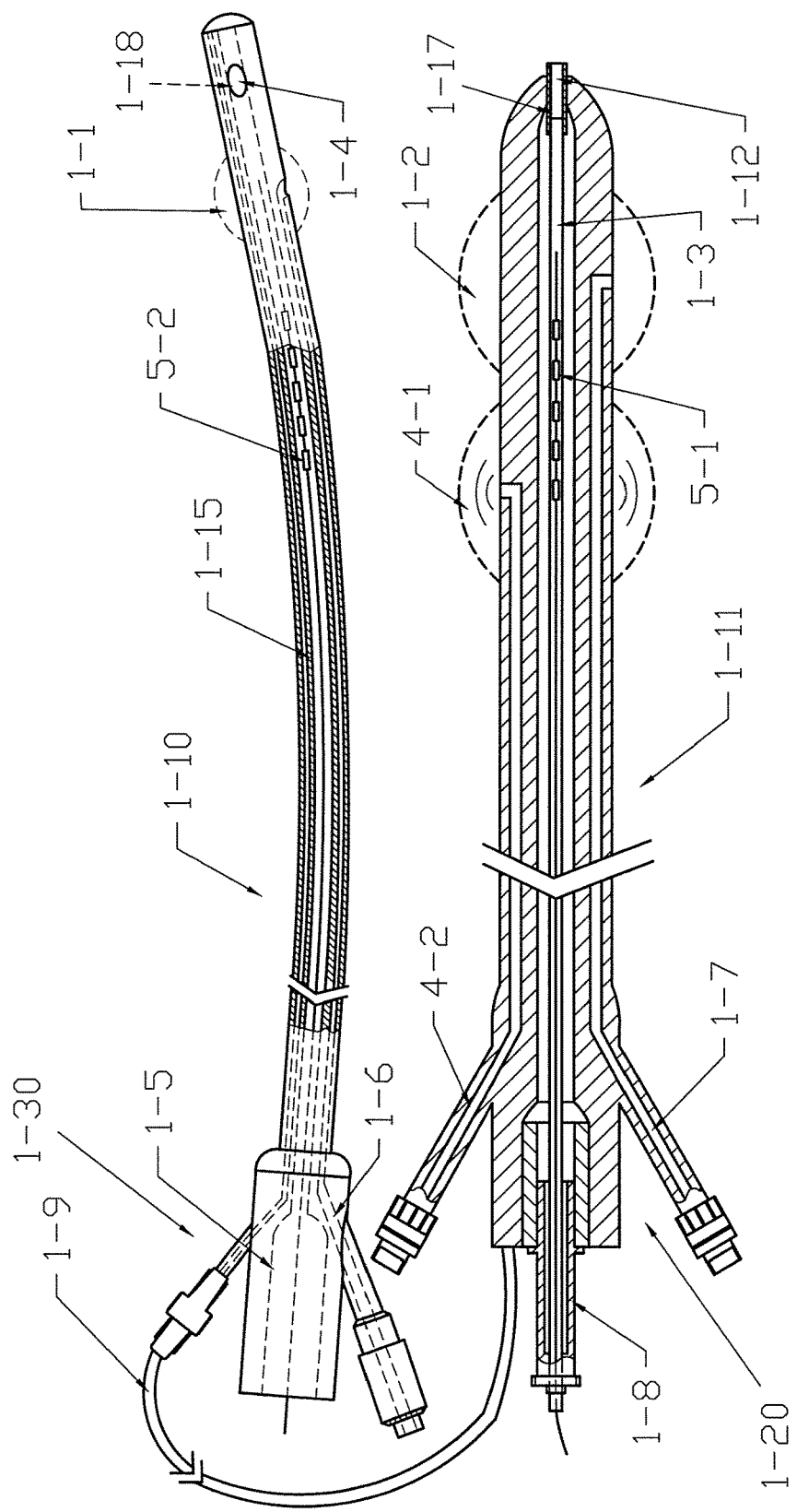
FIG. 4 is an illustration of a rectum catheter including a first position rectum balloon, a second position rectum balloon and a measuring device, such as a metal-oxide-semiconductor field-effect transistor (MOSFET), attached to a urethra catheter that includes a measuring device and a first position urethra catheter balloon.

FIG. 4 shows an exemplary medical device as a multi-balloon intra-cavity catheter, similar to that shown in FIG. 3, that includes a rectum catheter 1-11 attached to a urethra catheter 1-10. The rectum catheter 1-11 is a single intra-cavity multi-balloon catheter and includes a first position rectum balloon 1-2 and a second position rectum balloon 4-1, as well as a balloon inflator 1-20, as a multi-balloon inflator, having connections 1-7, 1-8 and 4-2, the plurality of inflatable balloons 1-2 and 4-1 being positioned on a same longitudinal axis of the rectum catheter 1-11, such as shown in FIG. 4; and the urethra catheter 1-10 includes a first position urethra catheter balloon 1-1, as well as a balloon inflator 1-30 having connections 1-5 and 1-6. The rectum catheter 1-11 may be attached by a locking mechanism 1-9 to the urethra catheter 1-10, as described. The rectum catheter 1-11 contains two balloons. The second position rectum balloon 4-1 contains radioactive isotopes, provided via the connection 4-2, while the first position rectum balloon 1-2 can contain air or liquid, such as a liquid saline solution, to fill the balloon via the connection 1-7. The rectum catheter 1-11 contains a measuring device 5-1 for dose measurement, as can be inserted through the connection 1-8 of a balloon inflator 1-20, similar to that previously described, that allows for measuring the dose that is applied to the patient. Next, a measuring device 5-2 for dose measurement, similar to that previously described, can also be inserted through an extraction opening connection 1-5 of a balloon inflator 1-30 and into an associated tube 1-15 of the urethra catheter 1-10, and along with the measuring device 5-1, as can be inserted through an extraction opening connection 1-8 of the balloon inflator 1-20 in the rectum catheter 1-11, can allow medical personnel to measure the dose from two different locations at the same time. Also, as described, the urethra catheter 1-10 has a urine or bodily fluid extraction opening 1-4 that is used to remove fluids in the bladder that are taken out by the extraction opening connection 1-5 of the balloon inflator 1-30 and into the associated tube 1-15 of the extraction opening connection 1-5. The extraction opening 1-4 contains an inner seal 1-18 that only allows for a single direction flow for removal of bodily fluids and does not allow for fluids to be inserted into a body cavity, such as the bladder. The rectum catheter 1-11 has the female or a male connection 1-8 of the balloon inflator 1-20, that can be used to insert any form of a sensor for dose measurement and simultaneously remove human waste by an extraction opening 1-12 in the rectum catheter 1-11. The extraction opening 1-12 contains an inner seal 1-17 that only allows for a single direction flow for removal of bodily fluids and does not allow for fluids to be inserted into a body cavity, such as the rectum. The human waste removed travels through a tube 1-3 associated with the male or female connection 1-8.

FIG. 5A shows an exemplary medical device, similar to those previously described, that includes a rectum catheter 1-11 attached to a urethra catheter 1-10. The urethra catheter 1-10 includes a first position urethra catheter balloon 1-1, as well as a balloon inflator 1-30 having connections 1-5 and 1-6. The rectum catheter 1-11 includes a first position rectum balloon 1-2, a second position radiation balloon 4-1, a third position rectum balloon 7-1 and is attached to the urethra catheter 1-10, as well as including a balloon inflator 1-20, as a multi-balloon inflator 1-20, having connections 1-7, 1-8, 7-3 and 4-2. The rectum catheter 1-11 may be attached by a locking mechanism 1-9 to the urethra catheter 1-10, as described. The rectum catheter 1-11 has three balloons 1-2, 4-1 and 7-1; however, there can be any number of balloons, as can be spaced from each other on the catheter 1-11, depending upon the length of the catheter 1-11. The rectum catheter 1-11 has the second position radiation balloon 4-1 that contains radioactive isotopes, inserted via the connection 4-2, while the first position rectum balloon 1-2 and the third position rectum balloon 7-1 may contain no dose delivery mechanism. The first position rectum balloon 1-2 can be inflated via the male/female connection 1-7, and the second position rectum balloon 4-1 can be inflated via the male/female connection 4-2. The third position rectum balloon 7-1 can be inflated via the male/female connection 7-3. Referring to FIG. 5B, an A-A view 7-2 of the rectum catheter 1-11 provides a further illustration of when there are a plurality of balloons on a single catheter, such as the rectum catheter 1-11. The A-A view 7-2 shows a cross-sectional view of the rectum catheter 1-11 and the respective tubes, or connections, 4-2, 7-3, 1-7 for inflating or deflating respective balloons, as well as the connection 1-8 that communicates with an opening 1-12. By having multiple balloons on a single catheter, the shape of each balloon can be changed relative to the location of the catheter, such as the rectum catheter 1-11, in the human body to allow for a proper fixture. Also, as described, the urethra catheter 1-10 has a urine or bodily fluid extraction opening 1-4 associated with a tube 1-15 that is used to remove fluids in the bladder that are taken out by an extraction opening connection 1-5 of the balloon inflator 1-30 and the associated tube 1-15. The extraction opening 1-4 contains an inner seal 1-18 that only allows for a single direction flow for removal of bodily fluids and does not allow for fluids to be inserted into a body cavity, such as the bladder. The rectum catheter 1-11 has the female or a male connection 1-8 of a balloon inflator 1-20, that can be used to insert any form of a sensor for dose measurement and simultaneously remove human waste by the opening 1-12 in the rectum catheter 1-11. The extraction opening 1-12 contains an inner seal 1-17 that only allows for a single direction flow for removal of bodily fluids and does not allow for fluids to be inserted into a body cavity, such as the rectum. The human waste removed travels through a tube 1-3 associated with the male or female connection 1-8.

FIG. 6A shows an exemplary medical device as a multi-balloon intra-cavity catheter, similar to that shown in FIG. 5A, that includes a rectum catheter 1-11 attached to a urethra catheter 1-10, as well as a balloon inflator 1-20, as a multi-balloon inflator, having connections 1-7, 1-8, 7-3 and 4-2. The urethra catheter 1-10 includes a first position urethra catheter balloon 1-1, as well as a balloon inflator 1-30 having connections 1-5 and 1-6. The rectum catheter 1-11 may be attached by a locking mechanism 1-9 to the urethra catheter 1-10, as described. The rectum catheter 1-11 is a single intra-cavity multi-balloon catheter and includes a collapsed first position rectum balloon 1-2 as a collapsed balloon 8-1 as can be inflated via the connection 1-7, a second position radiation balloon 4-1 as can be inflated or filled with a radioactive material, e.g. radioactive isotopes, via the connection 4-2 of the balloon inflator 1-20, and a third position rectum balloon 7-1 as can be inflated via the connection 7-3; and the balloons 1-2 (the collapsed balloon 8-1), 4-1 and 7-1 can be spaced from each other along the length of the catheter 1-11 and the plurality of inflatable balloons 1-2, 4-1 and 7-1 being positioned on a same longitudinal axis of the rectum catheter 1-11, such as illustrated in FIG. 6A. The collapsed balloon 8-1 allows for minimum expansion of the balloon, such as by inflation thereof via the connection 1-7, to keep the human tissue from being moved into any direction. Furthermore, a measuring device 8-2, similar to those previously described, can be inserted into an open section (tube) 1-3 associated with the connection 1-8 in the rectum catheter 1-11 of the balloon inflator 1-20. The benefit for having multiple balloons allows the control of how much dose can be given. Next, a measuring device 8-3, similar to those previously described, can also be inserted into the urethra catheter 1-10 through an extraction opening connection 1-5 of the balloon inflator 1-30 and into an associated tube 1-15 of the extraction opening connection 1-5, along with a measuring device 8-2, in the rectum catheter 1-11 to allow medical personnel to measure the dose from two different locations at the same time. Referring to FIG. 6B, an A-A view 7-2 of the rectum catheter 1-11 provides a further illustration of when a plurality of balloons are on a single catheter, such as the rectum catheter 1-11. The A-A view 7-2 shows a cross-sectional view of the rectum catheter 1-11 and the respective tubes, or connections, 4-2, 7-3, 1-7 for inflating or deflating the respective balloons, as well as the connection 1-8 that communicates with an extraction opening 1-12. By having multiple balloons on a single catheter, the shape of each balloon can be changed relative to the location of the catheter, such as the rectum catheter 1-11, in the human body to allow for a proper fixture. The advantage for having multiple balloons allows medical personnel to have more control. Also, as described, the urethra catheter 1-10 has a urine or bodily fluid extraction opening 1-4 that is used to remove fluids in the bladder that are taken out by the extraction opening connection 1-5 of the balloon inflator 1-30 and by the associated tube 1-15. The extraction opening 1-4 contains an inner seal 1-18 that only allows for a single direction flow for removal of bodily fluids and does not allow for fluids to be inserted into a body cavity, such as the bladder. The rectum catheter 1-11 has the female or a male connection 1-8 of the balloon inflator 1-20, that can be used to insert any form of a sensor for dose measurement and simultaneously remove human waste by the extraction opening 1-12 in the rectum catheter 1-11. The extraction opening 1-12 contains an inner seal 1-17 that only allows for a single direction flow for removal of bodily fluids and does not allow for fluids to be inserted into a body cavity, such as the rectum. The human waste removed travels through a tube 1-3 associated with the male or female connection 1-8.

Figure 7:
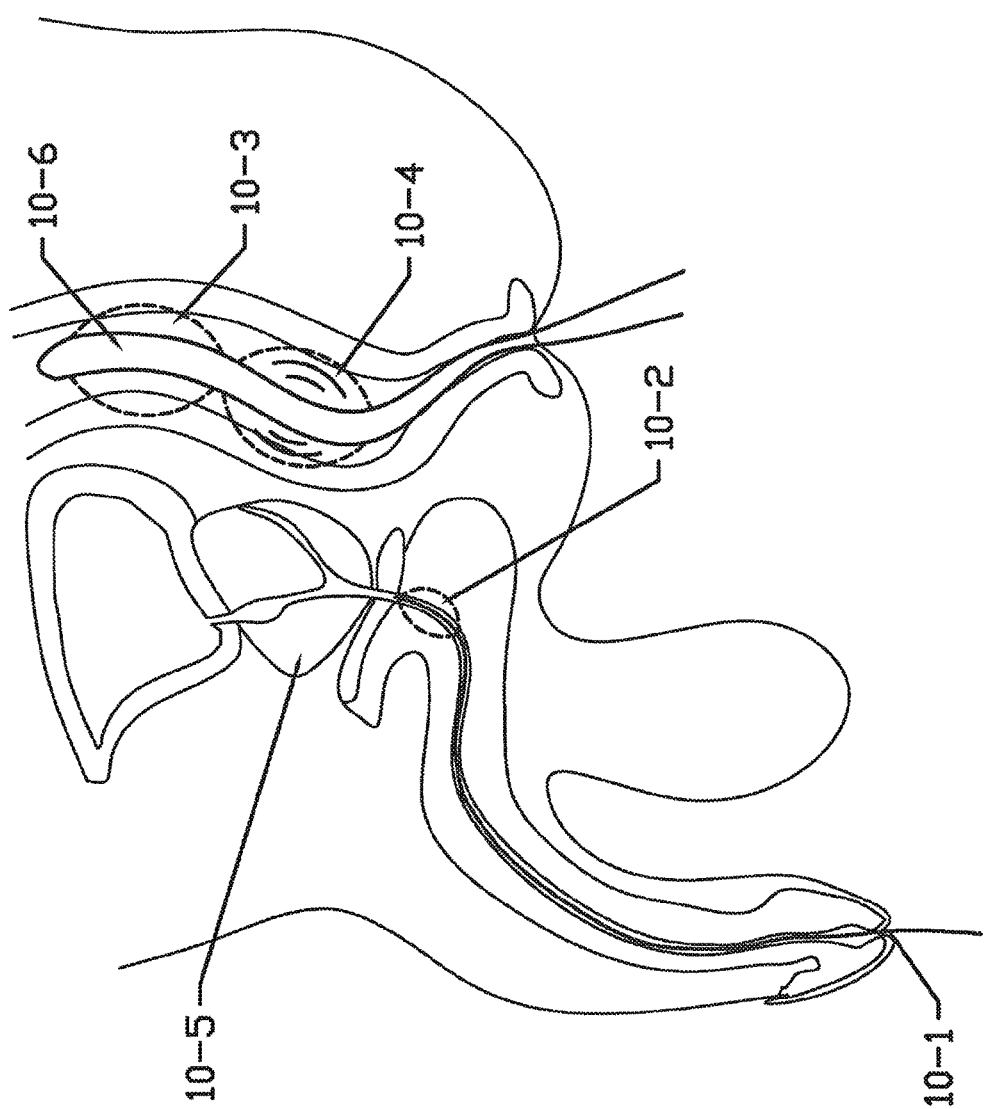
FIG. 7 is an illustration of a first position rectum balloon and a second position rectum balloon in the human body and a first position urethra catheter balloon in the human body.

FIG. 7 is an illustration of how both a urethra catheter 10-1 and a rectum catheter 10-6 are inserted into the human body. The urethra catheter 10-1 is inserted into the penis via the urethra. Thereafter, the medical personnel inflate a balloon 10-2 on the urethra catheter 10-1. This will allow the surrounding tissue to expand and move out of the way to create space near the prostate 10-5. Furthermore, the rectum catheter 10-6 can be inserted into the rectum of the patient. The rectum catheter 10-6 has a first position rectum balloon 10-3 and a second position rectum balloon 10-4. Looking specifically at this illustration of FIG. 7, but not limiting it to just the second position rectum balloon 10-4, the second position rectum balloon 10-4 contains radioactive isotopes. This can be used to dose the prostate 10-5, and the first position rectum balloon 10-3 can be used as a locking or fixing mechanism to hold the rectum catheter 10-6 in place. Furthermore, a measuring device for dose measurement, similar to those previously described, can be inserted into both the urethra catheter 10-1 and the rectum catheter 10-6.

FIG. 8 is another illustration of how both the urethra catheter 10-1 and the rectum catheter 10-6 are inserted into the human body. The urethra catheter 10-1 is inserted all the way into the male bladder and inflated with a balloon 11-1. The inflation of the balloon 11-1 will not allow for the urethra catheter 10-1 to slip out of the bladder. Furthermore, the rectum catheter 10-6 has a first position rectum balloon 10-3 and a second position rectum balloon 10-4. Looking specifically at this illustration of FIG. 8, but not limiting it to just the second position rectum balloon 10-4, the second position rectum balloon 10-4 contains radioactive isotopes. This second position rectum balloon 10-4 can be used to dose the prostate 10-5, and the first position rectum balloon 10-3 can be used as a locking or fixing mechanism to hold the rectum catheter 10-6 in place. Furthermore, a measuring device for dose measurement, similar to those previously described, can be inserted into both the urethra catheter 10-1 and the rectum catheter 10-6.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

Further, the particular features presented in the dependent claims can be combined with each other in other manners within the scope of the invention such that the invention should be recognized as also specifically directed to other embodiments having any other possible combination of the features of the dependent claims.

With this description, those skilled in the art may recognize other equivalents to the specific embodiments described herein. Such equivalents are intended to be encompassed by the claims attached hereto.

The invention claimed is:

1. A multi-balloon intra-cavity catheter for a medical application, comprising:
    a single intra-cavity catheter configured for insertion into a body cavity for the medical application;
    a plurality of inflatable balloons associated with the single intra-cavity catheter, the plurality of inflatable balloons being positioned on a same longitudinal axis of the single intra-cavity catheter, the plurality of inflatable balloons each being configured to be filled with a liquid or air to selectively fix or position the single intra-cavity catheter in the body cavity or to be filled with a radioactive material to selectively deliver by the radioactive material a radiation dose to tissue, each of the plurality of inflatable balloons being configured to be positioned spaced from each other in a non-overlapping contiguous arrangement on the same longitudinal axis of the single intra-cavity catheter;
    a multi-balloon inflator that selectively inflates the plurality of inflatable balloons associated with the single intra-cavity catheter with the liquid, the air or the radioactive material; and
    a plurality of connections associated with the multi-balloon inflator and configured to enable insertion of the liquid, the air or the radioactive material into corresponding ones of the plurality of inflatable balloons through the multi-balloon inflator, the plurality of connections being configured to respectively inflate each of the plurality of inflatable balloons to a corresponding size or shape relative to a location of the single intra-cavity catheter while the single intra-cavity catheter is positioned in the body cavity for the medical application.

2. The multi-balloon intra-cavity catheter for a medical application of claim 1, further comprising:
    an extraction opening connection associated with the multi-balloon inflator in communication with an extraction opening of the single intra-cavity catheter configured to remove bodily fluid from the body cavity while the single intra-cavity catheter is positioned in the body cavity, the extraction opening connection having an associated tube configured to communicate with the extraction opening for removal of the bodily fluid from the body cavity.

3. The multi-balloon intra-cavity catheter for a medical application of claim 1, further comprising:
    an extraction opening connection associated with the multi-balloon inflator in communication with an extraction opening of the single intra-cavity catheter configured to remove a bodily fluid from the body cavity while the single intra-cavity catheter is positioned in the body cavity, the extraction opening connection having an associated tube configured to communicate with the extraction opening for removal of the bodily fluid from the body cavity, the extraction opening connection and the associated tube being configured to contain a measuring device used to measure an amount of a radiation dose radiated to tissue during inclusion of the radioactive material in at least one of the plurality of inflatable balloons while the extraction opening connection through the associated tube and the extraction opening removes the bodily fluid from the body cavity.

4. The multi-balloon intra-cavity catheter for a medical application of claim 3, wherein:
    the radioactive material comprises radioactive isotopes.

5. The multi-balloon intra-cavity catheter for a medical application of claim 1, wherein:
    the radioactive material comprises radioactive isotopes.

6. The multi-balloon intra-cavity catheter for a medical application of claim 1, wherein:
    at least one of the plurality of inflatable balloons is configured to include the radioactive material, and
    the single intra-cavity catheter is configured to receive a measuring device configured to take dose measurements while applying radiation dose therapy during inclusion of the radioactive material in at least one of the plurality of inflatable balloons.

7. The multi-balloon intra-cavity catheter for a medical application of claim 1, wherein:
the plurality of inflatable balloons comprises at least two inflatable balloons to selectively fix or position the single intra-cavity catheter in the body cavity.

8. The multi-balloon intra-cavity catheter for a medical application of claim 7, further comprising:
a measuring device positioned in association with the single intra-cavity catheter to take dose measurements while applying radiation dose therapy during inclusion of the radioactive material in at least one of the plurality of inflatable balloons.

9. The multi-balloon intra-cavity catheter for a medical application of claim 8, wherein:
the measuring device comprises a metal-oxide-semiconductor field-effect transistor (MOSFET).

10. The multi-balloon intra-cavity catheter for a medical application of claim 9, wherein:
the radioactive material comprises radioactive isotopes.

11. The multi-balloon intra-cavity catheter for a medical application of claim 1, further comprising:
an extraction opening connection associated with the multi-balloon inflator in communication with an extraction opening of the single intra-cavity catheter configured to remove a bodily fluid from the body cavity while the single intra-cavity catheter is positioned in the body cavity, the extraction opening connection having an associated tube configured to communicate with the extraction opening for removal of the bodily fluid from the body cavity,
wherein the extraction opening of the single intra-cavity catheter includes an inner seal that allows for a single direction of flow for removal of the bodily fluid from the body cavity.

12. The multi-balloon intra-cavity catheter for a medical application of claim 1, wherein:
the plurality of connections associated with the multi-balloon inflator are configured in communicating relation with the plurality of inflatable balloons to enable selectively controlling the size of each of the plurality of inflatable balloons independently of the size of one or more of other of the plurality of inflatable balloons.

13. The multi-balloon intra-cavity catheter for a medical application of claim 12, wherein:
the plurality of connections associated with the multi-balloon inflator are configured in communicating relation with the plurality of inflatable balloons to enable selectively changing the shape of each of the plurality of inflatable balloons independently of the shape of one or more of other of the plurality of inflatable balloons.

14. The multi-balloon intra-cavity catheter for a medical application of claim 1, wherein:
the plurality of connections associated with the multi-balloon inflator are configured in communicating relation with the plurality of inflatable balloons to enable selectively changing the shape of each of the plurality of inflatable balloons independently of the shape of one or more of other of the plurality of inflatable balloons.

15. A multi-balloon intra-cavity catheter for a medical application, comprising:
a single intra-cavity catheter configured for insertion into a body cavity for the medical application;
a plurality of inflatable balloons associated with the single intra-cavity catheter, the plurality of inflatable balloons each being configured to be filled with a liquid or air to selectively fix or position the single intra-cavity catheter in the body cavity, each of the plurality of inflatable balloons being configured to be positioned spaced from each other in a non-overlapping contiguous arrangement on a same longitudinal axis of the single intra-cavity catheter;
a multi-balloon inflator that selectively inflates the plurality of inflatable balloons associated with the single intra-cavity catheter with the liquid or the air; and
a plurality of connections associated with the multi-balloon inflator and configured to selectively enable insertion of the liquid or the air into corresponding ones of the plurality of inflatable balloons through the multi-balloon inflator, the plurality of connections being configured to respectively inflate each of the plurality of inflatable balloons to a corresponding size or shape relative to a location of the single intra-cavity catheter while the single intra-cavity catheter is positioned in the body cavity for the medical application.

16. The multi-balloon intra-cavity catheter for a medical application of claim 15, further comprising:
an extraction opening connection associated with the multi-balloon inflator in communication with an extraction opening of the single intra-cavity catheter configured to remove a bodily fluid from the body cavity while the single intra-cavity catheter is positioned in the body cavity, the extraction opening connection having an associated tube configured to communicate with the extraction opening for removal of the bodily fluid from the body cavity.

17. The multi-balloon intra-cavity catheter for a medical application of claim 16, wherein:
the extraction opening of the single intra-cavity catheter includes an inner seal that allows for a single direction of flow for removal of the bodily fluid from the body cavity.

18. The multi-balloon intra-cavity catheter for a medical application of claim 15, further comprising:
a measuring device positioned in association with the single intra-cavity catheter to take dose measurements while applying radiation dose therapy.

19. The multi-balloon intra-cavity catheter for a medical application of claim 18, wherein:
the measuring device comprises a metal-oxide-semiconductor field-effect transistor (MOSFET).

20. The multi-balloon intra-cavity catheter for a medical application of claim 15, wherein:
the plurality of connections associated with the multi-balloon inflator are configured in communicating relation with the plurality of inflatable balloons to enable selectively controlling the size of each of the plurality of inflatable balloons independently of the size of one or more of other of the plurality of inflatable balloons.

21. The multi-balloon intra-cavity catheter for a medical application of claim 20, wherein:
the plurality of connections associated with the multi-balloon inflator are configured in communicating relation with the plurality of inflatable balloons to enable selectively changing the shape of each of the plurality of inflatable balloons independently of the shape of one or more of other of the plurality of inflatable balloons.

22. The multi-balloon intra-cavity catheter for a medical application of claim 15, wherein:
the plurality of connections associated with the multi-balloon inflator are configured in communicating relation with the plurality of inflatable balloons to enable selectively changing the shape of each of the plurality of inflatable balloons independently of the shape of one or more of other of the plurality of inflatable balloons.

23. The multi-balloon intra-cavity catheter for a medical application of claim 15, further comprising:
at least one second inflatable balloon configured to be positioned spaced from the plurality of inflatable balloons on the same longitudinal axis of the single intra-cavity catheter and configured to be filled with a radioactive material to deliver a radiation dose to tissue,
wherein the multi-balloon inflator selectively inflates the plurality of first inflatable balloons with the liquid or the air and selectively inflates the at least one second inflatable balloon with the radioactive material in association with the plurality of connections, each of the plurality of connections respectively communicating with a corresponding one of the plurality of inflatable balloons to provide the liquid or the air to the corresponding one of the plurality of inflatable balloons and respectively communicating with the at least one second inflatable balloon to selectively provide the radioactive material to a corresponding said at least one second inflatable balloon.

24. The multi-balloon intra-cavity catheter for a medical application of claim 23, further comprising:
an extraction opening connection associated with the multi-balloon inflator in communication with an extraction opening of the single intra-cavity catheter configured to remove a bodily fluid from the body cavity while the single intra-cavity catheter is positioned in the body cavity, the extraction opening connection having an associated tube configured to communicate with the extraction opening for removal of the bodily fluid from the body cavity, the extraction opening connection and the associated tube being configured to contain a measuring device to measure an amount of the radiation dose radiated to the tissue during inclusion of the radioactive material in the at least one second inflatable balloon while the extraction opening connection through the associated tube and the extraction opening removes the bodily fluid from the body cavity.

25. The multi-balloon intra-cavity catheter for a medical application of claim 24, wherein:
the radioactive material comprises radioactive isotopes.

26. The multi-balloon intra-cavity catheter for a medical application of claim 24, further comprising:
the measuring device positioned in association with the single intra-cavity catheter to take dose measurements while applying radiation dose therapy.

27. The multi-balloon intra-cavity catheter for a medical application of claim 26, wherein:
the measuring device comprises a metal-oxide-semiconductor field-effect transistor (MOSFET).

28. The multi-balloon intra-cavity catheter for a medical application of claim 24, wherein:
the extraction opening of the single intra-cavity catheter includes an inner seal that allows for a single direction of flow for removal of the bodily fluid from the body cavity.

29. The multi-balloon intra-cavity catheter for a medical application of claim 23, wherein:
the plurality of connections associated with the multi-balloon inflator are configured in communicating relation with the plurality of inflatable balloons and in communicating relation with the at least one second inflatable balloon to enable selectively controlling the size of each of the plurality of inflatable balloons independently of the size of the at least one second inflatable balloon.

30. The multi-balloon intra-cavity catheter for a medical application of claim 29, wherein:
the plurality of connections associated with the multi-balloon inflator are configured in communicating relation with the plurality of inflatable balloons and in communicating relation with the at least one second inflatable balloon to enable selectively changing the shape of each of the plurality of inflatable balloons independently of the shape of the at least one second inflatable balloon.

31. The multi-balloon intra-cavity catheter for a medical application of claim 23, wherein:
the plurality of connections associated with the multi-balloon inflator are configured in communicating relation with the plurality of inflatable balloons and in communicating relation with the at least one second inflatable balloon to enable selectively changing the shape of each of the plurality of inflatable balloons independently of the shape of the at least one second inflatable balloon.

32. The multi-balloon intra-cavity catheter for a medical application of claim 15, further comprising:
at least one second inflatable balloon configured to be positioned spaced from the plurality of inflatable balloons on the same longitudinal axis of the single intra-cavity catheter and configured to be filled with a radioactive material to deliver a radiation dose to tissue,
wherein the plurality of inflatable balloons includes a pair of inflatable balloons, one inflatable balloon of the pair of inflatable balloons being positioned in spaced opposing relation on the same longitudinal axis of the single intra-cavity catheter to one side of the at least one second inflatable balloon and the other inflatable balloon of the pair of inflatable balloons being positioned in spaced opposing relation to the other side of the at least one second inflatable balloon on the same longitudinal axis of the single intra-cavity catheter, and
wherein the multi-balloon inflator in association with the plurality of connections selectively inflates the plurality of inflatable balloons and selectively inflates the at least one second inflatable balloon, each of the plurality of connections respectively communicating with a corresponding one of the plurality of inflatable balloons to provide the liquid or the air to the corresponding one of the plurality of inflatable balloons and respectively communicating with the at least one second inflatable balloon to selectively provide the radioactive material to a corresponding said at least one second inflatable balloon.

33. The multi-balloon intra-cavity catheter for a medical application of claim 32, wherein:
the plurality of connections associated with the multi-balloon inflator are configured in communicating relation with the pair of inflatable balloons and in communicating relation with the at least one second inflatable balloon to enable selectively controlling the size of the pair of inflatable balloons independently of the size of the at least one second inflatable balloon.

34. The multi-balloon intra-cavity catheter for a medical application of claim 32, wherein:
the plurality of connections associated with the multi-balloon inflator are configured in communicating relation with the pair of inflatable balloons and in communicating relation with the at least one second inflatable balloon to enable selectively changing the shape of the pair of inflatable balloons independently of the shape of the at least one second inflatable balloon.

* * * * *